(12) United States Patent
Park et al.

(10) Patent No.: US 12,274,535 B2
(45) Date of Patent: Apr. 15, 2025

(54) APPARATUS AND METHOD FOR ESTIMATING BLOOD PRESSURE

(71) Applicant: SAMSUNG ELECTRONICS CO., LTD., Suwon-si (KR)

(72) Inventors: Chang Soon Park, Chungju-si (KR); Ui Kun Kwon, Hwaseong-si (KR); Young Soo Kim, Seoul (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 521 days.

(21) Appl. No.: 17/839,722

(22) Filed: Jun. 14, 2022

(65) Prior Publication Data

US 2023/0190118 A1  Jun. 22, 2023

(30) Foreign Application Priority Data

Dec. 20, 2021  (KR) ........................ 10-2021-0183193

(51) Int. Cl.
*A61B 5/021* (2006.01)
*A61B 5/00* (2006.01)
*A61B 5/024* (2006.01)

(52) U.S. Cl.
CPC ...... *A61B 5/02125* (2013.01); *A61B 5/02416* (2013.01); *A61B 5/681* (2013.01)

(58) Field of Classification Search
CPC . A61B 5/02125; A61B 5/02416; A61B 5/681; A61B 5/0075; A61B 5/02438;
(Continued)

(56) References Cited

U.S. PATENT DOCUMENTS

| 11,123,022 B2 | 9/2021 | Kwon et al. |
| 11,284,843 B2 | 3/2022 | Park et al. |

(Continued)

FOREIGN PATENT DOCUMENTS

| EP | 3 476 283 A1 | 5/2019 |
| KR | 10-1503604 B1 | 3/2015 |

(Continued)

OTHER PUBLICATIONS

Yoon, Youngzoon et al., "Nonconstrained Blood Pressure Measurement By Photoplethysmography", Journal of the Optical Society of Korea, vol. 10, No. 2, Jun. 2006, pp. 91-95. (5 pages total).

(Continued)

*Primary Examiner* — Peter Luong
(74) *Attorney, Agent, or Firm* — Sughrue Mion, PLLC

(57) ABSTRACT

An apparatus for estimating blood pressure may include: a memory storing one or more instructions; and a processor configured to execute the one or more instructions to: extract a cardiac output (CO) feature, a first candidate total peripheral resistance (TPR) feature, and a second candidate TPR feature from a bio-signal; determine one of the first candidate TPR feature and the second candidate TPR feature as a TPR feature based on a direction of change in the CO feature and a direction of change in the first candidate TPR feature between a blood pressure measurement time and a calibration time; and estimate the blood pressure based on the TPR feature and the CO feature.

20 Claims, 16 Drawing Sheets

(58) Field of Classification Search
CPC . A61B 5/6898; A61B 5/6815; A61B 5/02028; A61B 5/02108; A61B 5/7278; A61B 5/029; A61B 5/021; A61B 5/0225; A61B 5/389; A61B 5/72; A61B 5/02116; A61B 5/7221; A61B 5/02427; A61B 5/0245; A61B 5/14552; A61B 2562/00; A61B 5/024; A61B 5/0205; A61B 8/02; A61B 5/02

See application file for complete search history.

(56) References Cited

U.S. PATENT DOCUMENTS

| | | | |
|---|---|---|---|
| 11,426,130 | B2 | 8/2022 | Jang et al. |
| 2016/0081563 | A1* | 3/2016 | Wiard .................. A61B 5/7278 600/485 |
| 2016/0270668 | A1 | 9/2016 | Gil |
| 2018/0177466 | A1 | 6/2018 | Park et al. |
| 2019/0110757 | A1* | 4/2019 | Kwon ................ A61B 5/02116 |
| 2020/0054223 | A1 | 2/2020 | Kwon et al. |
| 2020/0054290 | A1* | 2/2020 | Jang .................... A61B 5/1102 |
| 2020/0077904 | A1 | 3/2020 | Kang et al. |
| 2020/0229743 | A1 | 7/2020 | Choi et al. |
| 2020/0275839 | A1 | 9/2020 | Park et al. |
| 2020/0397309 | A1 | 12/2020 | Jang et al. |
| 2021/0085259 | A1 | 3/2021 | Kwon et al. |
| 2021/0228100 | A1 | 7/2021 | Park et al. |
| 2021/0282648 | A1 | 9/2021 | Park et al. |
| 2021/0378602 | A1 | 12/2021 | Kwon et al. |
| 2022/0008020 | A1 | 1/2022 | Park et al. |
| 2022/0031175 | A1 | 2/2022 | Kang et al. |

FOREIGN PATENT DOCUMENTS

| | | |
|---|---|---|
| KR | 10-2018-0077019 A | 7/2018 |
| KR | 10-2019-0043453 A | 4/2019 |
| KR | 10-2019-0100020 A | 8/2019 |
| KR | 10-2020-0021207 A | 2/2020 |
| KR | 10-2020-0021208 A | 2/2020 |
| KR | 10-2020-0029907 A | 3/2020 |
| KR | 10-2020-0091625 A | 7/2020 |
| KR | 10-2020-0105212 A | 9/2020 |
| KR | 10-2020-0144688 A | 12/2020 |
| KR | 10-2021-0033789 A | 3/2021 |
| KR | 10-2021-0114228 A | 9/2021 |

OTHER PUBLICATIONS

Millasseau, Sandrine C et al., "The Vascular Impact of Aging and Vasoactive Drugs: Comparison of Two Digital Volume Pulse Measurements", AJH, 2003, vol. 16, pp. 467-472. (6 pages total).

Yanjun Li et al., "Characters available in photoplethysmogram for blood pressure estimation: beyond the pulse transit time", Australasian Physical & Engineering Sciences in Medicine, Apr. 11, 2014, vol. 37, Issue 2, pp. 367-376, DOI: 10.1007/s13246-014-0269-6, XP035317069.

Communication issued on Aug. 30, 2023 by the European Patent Office for European Patent Application No. 22203545.3.

Office Action dated Sep. 21, 2023, issued by Korean Patent Office in Korean Patent Application No. 10-2021-0183193.

* cited by examiner

APPARATUS AND METHOD FOR ESTIMATING BLOOD PRESSURE

CROSS-REFERENCE TO RELATED APPLICATION(S)

This application claims priority from Korean Patent Application No. 10-2021-0183193, filed on Dec. 20, 2021, in the Korean Intellectual Property Office, the entire disclosure of which is incorporated herein by reference for all purposes.

BACKGROUND

1. Field

One or more example embodiments relate to estimating blood pressure based on features extracted from a pulse wave signal.

2. Description of the Related Art

Research on information technology (IT)-medical convergence technology, in which IT and medical technology are combined, is being recently carried out to address the aging population structure, rapid increase in medical expenses, and shortage of specialized medical service personnel. Particularly, monitoring of the health condition of the human body is not limited to a fixed place, such as a hospital, but is expanding to a mobile healthcare sector for monitoring a user's health status at any time and any place in daily life at home and office. Electrocardiography (ECG), photoplethysmogram (PPG), and electromyography (EMG) signals are examples of bio-signals that indicate the individual's health condition. A variety of signal sensors are being developed to measure such signals in daily life. Especially, in the case of a PPG sensor, it is possible to estimate blood pressure of a human body by analyzing a form of pulse wave that reflects a cardiovascular state.

A PPG signal is a summation of a propagation wave propagating from the heart to peripheral parts of a body and reflection waves returning from the peripheral parts of the body. It is known that information to be used to estimate blood pressure can be acquired by extracting various features related to propagation waves or reflection waves.

SUMMARY

According to an aspect of the present disclosure, an apparatus for estimating blood pressure may include: a memory storing one or more instructions; and a processor configured to execute the one or more instructions to: extract a cardiac output (CO) feature, a first candidate total peripheral resistance (TPR) feature, and a second candidate TPR feature from a bio-signal; determine one of the first candidate TPR feature and the second candidate TPR feature as a TPR feature based on a direction of change in the CO feature and a direction of change in the first candidate TPR feature between a blood pressure measurement time and a calibration time; and estimate the blood pressure based on the TPR feature and the CO feature.

The CO feature may include at least one of a heart rate, and a ratio between an amplitude at a predetermined point and an area under a waveform of the bio-signal.

The predetermined point may include a point at which a slope of the waveform of the bio-signal is closest to zero in a systolic phase.

The first candidate TPR feature may include a ratio between an amplitude of a propagation wave component and an amplitude of a reflection wave component of the bio-signal. The second candidate TPR feature may include a ratio between the amplitude of the reflection wave component and an amplitude at an internally dividing point between a point of the propagation wave component and a predetermined point of the bio-signal.

The processor may be further configured to obtain a second derivative signal of the bio-signal; and detect local minimum points of the second derivative signal as the point of the propagation wave component and a point of the reflection wave component.

In response to the direction of change in the CO feature being different from the direction of change in the first candidate TPR feature, the processor may be further configured to determine the first candidate TPR feature as the TPR feature, and in response to the directions of change being identical, the processor may be further configured to determine the second candidate TPR feature as the TPR feature.

In response to the direction of change in the CO feature being different from the direction of change in the first candidate TPR feature, and a variation in the first candidate TPR feature being less than a predetermined threshold value, the processor may be further configured to determine the first candidate TPR feature as the TPR feature. In response to the direction of change in the CO feature being different from the direction of change in the first candidate TPR feature, and the variation in the first candidate TPR feature being greater than or being equal to the predetermined threshold value, the processor may be further configured to determine the second candidate TPR feature as the TPR feature. In response to the direction of change in the CO feature being identical to the direction of change in the first candidate TPR feature, the processor may be further configured to determine the second candidate TPR feature as the TPR feature.

The predetermined threshold value may include a value obtained by applying a predetermined weight to a variation in the CO feature.

The processor may be further configured to determine: the variation in the first candidate TPR feature by dividing the first candidate TPR feature value at the blood pressure measurement time by a reference TPR feature value at the calibration time, to obtain a first division result, and by subtracting 1 from the first division result; and the variation in the CO feature by dividing the CO feature value at the blood pressure measurement time by a reference CO feature value at the calibration time, to obtain a second division result, and by subtracting 1 from the second division result.

The processor may be further configured to estimate the blood pressure by applying a predefined blood pressure estimation model to a result obtained by combining the CO feature and the TPR feature.

According to another aspect of the present disclosure, a method of estimating blood pressure, may include: measuring a bio-signal from an object; extracting a cardiac output (CO) feature, a first candidate total peripheral resistance (TPR) feature, and a second candidate TPR feature based on the bio-signal; determining one of the first candidate TPR feature and the second candidate TPR feature as a TPR feature based on a direction of change in the CO feature and a direction of change in the first candidate TPR feature between a blood pressure measurement time and a calibration time; and estimating the blood pressure based on the TPR feature and the CO feature.

The CO feature may include at least one of a heart rate, and a ratio between an amplitude at a predetermined point and an area under a waveform of the bio-signal.

The predetermined point may include a point at which a slope of the waveform of the bio-signal is closest to zero in a systolic phase.

The first candidate TPR feature may include a ratio between an amplitude of a propagation wave component and an amplitude of a reflection wave component of the bio-signal. The second candidate TPR feature may include a ratio between the amplitude of the reflection wave component and an amplitude at an internally dividing point between a point of the propagation wave component and a predetermined point of the bio-signal.

The determining of the TPR feature may include, in response to the direction of change in the CO feature being different from the direction of change in the first candidate TPR feature, determining the first candidate TPR feature as the TPR feature, and in response to the directions of change being identical, determining the second candidate TPR feature as the TPR feature.

The determining of the TPR feature may include: in response to the direction of change in the CO feature being different from the direction of change in the first candidate TPR feature, and a variation in the first candidate TPR feature being less than a predetermined threshold value, determining the first candidate TPR feature as the TPR feature; in response to the direction of change in the CO feature being different from the direction of change in the first candidate TPR feature, and the variation in the first candidate TPR feature being greater than or being equal to the predetermined threshold value, determining the second candidate TPR feature as the TPR feature; and in response to the direction of change in the CO feature being identical to the direction of change in the first candidate TPR feature, determining the second candidate TPR feature as the TPR feature.

The predetermined threshold value may include a value obtained by applying a predetermined weight to the variation in the CO feature.

The estimating of the blood pressure may include estimating the blood pressure by applying a predefined blood pressure estimation model to a result obtained by combining the CO feature and the TPR feature.

According to another aspect of the present disclosure, an electronic device may include: a main body; a photoplethysmogram (PPG) sensor configured to measure a PPG signal from an object; and a processor configured to: extract a cardiac output (CO) feature and a first candidate total peripheral resistance (TPR) feature from the PPG signal; determine a TPR feature based on whether a direction of change in the CO feature is identical to a direction of change in the first candidate TPR feature between a blood pressure measurement time and a calibration time; and estimate blood pressure based on the TPR feature and the CO feature.

In response to the direction of change in the CO feature being different from the direction of change in the first candidate TPR feature, the processor may be further configured to determine the first candidate TPR feature as the TPR feature, and in response to the directions of change being identical, the processor may be further configured to extract a second candidate TPR feature, having a less variation than the first candidate TPR feature between the blood pressure measurement time and the calibration time, as the TPR feature.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
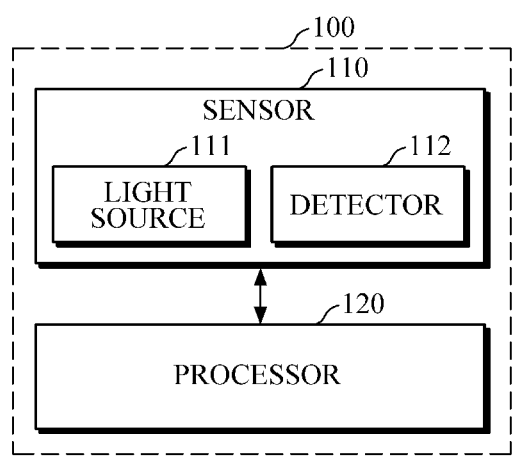
FIG. 1 is a block diagram illustrating an apparatus for estimating blood pressure according to an example embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as "unit" or "module", etc., should be understood as a unit for performing at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

FIG. 1 is a block diagram illustrating an apparatus for estimating blood pressure according to an example embodiment of the present disclosure.

Referring to FIG. 1, an apparatus 100 for estimating blood pressure includes a sensor 110 and a processor 120.

The sensor 110 may acquire a bio-signal from an object and may transmit the acquired bio-signal to the processor 120. In particular, the bio-signal may include various bio-signals, such as an Electrocardiography (ECG) signal, a Photoplethysmogram (PPG) signal, an Electromyography (EMG) signal, etc., which may be modeled by a summation of a plurality of waveform components. The sensor 110 may include a PPG sensor, an ECG sensor, and an EMG sensor to estimate blood pressure of a human body by analyzing a form of a pulse wave signal that reflects a cardiovascular state.

For example, the sensor 110 may be a spectrometer or a PPG sensor for measuring a PPG signal, and as illustrated herein, the sensor 110 may include a light source 111 for emitting light onto an object and a detector 112 for detecting light returning from body tissue of the object by being scattered or reflected from or transmitted into the body tissue after light is emitted by the light source 111 onto the object. The light source 111 may be formed as one or more light sources or an array of light sources, and the respective light sources may be formed as a light emitting diode (LED), a laser diode (LD), a phosphor, and the like. The plurality of light sources may emit light of different wavelengths, e.g., red, green, blue, infrared wavelengths, etc., with no specific limitation thereon. The plurality of light sources may be driven simultaneously or may be sequentially driven in a time-division manner. The detector 112 may include a photodiode, a photo transistor, an image sensor (e.g., complementary metal-oxide semiconductor (CMOS) image sensor), a spectrometer, and the like. The detector 112 may be formed as one or more detectors or an array of detectors.

The sensor 110 may measure a bio-signal from the object under the control of the processor 120. The sensor 110 may continuously measure bio-signals during a predetermined period of time when a user places the object on the sensor 110 and gradually increases or decreases a pressing force. The object may be a body part that may come into contact with the sensor 110, and may be, for example, a body part where pulse waves may be easily measured. For example, the object may be a surface of the wrist that is adjacent to the radial artery and an upper part of the wrist where venous blood or capillary blood passes. When a pulse wave is measured on a skin surface of the wrist under which the radial artery passes, the influence of external factors, such as the thickness of the skin tissue inside the wrist, which cause a measurement error can be relatively small. However, the object is not limited to the above examples, and may be a peripheral region of a human body, such as a finger, a toe, or the like, which is a region having a high blood vessel density in the human body.

A force sensor for measuring a change in force, applied by the object to the sensor 110, may be disposed at an upper end or a lower end of the sensor 110. Here, the force sensor may refer to a pressure sensor, and the force measured by the force sensor may also refer to pressure.

The processor 120 may control the sensor 110 upon receiving a request for estimating blood pressure from a user or an external device. When the force sensor measures the pressing force applied by the object to the sensor 110, the processor 120 may guide the user to apply appropriate pressure based on the measured force.

The processor 120 may be electrically or functionally connected to the sensor 110 and may control the sensor 110 to acquire a bio-signal. Upon receiving the bio-signal from the sensor 110, the processor 120 may perform preprocessing, such as filtering for removing noise from the received signal. For example, the processor 120 may perform signal correction, such as filtering (e.g., band-pass filtering between 0.4 Hz and 10 Hz), amplification of the bio-signal, converting the signal into a digital signal, smoothing, ensemble averaging of continuously measured bio-signals, and the like. In addition, one representative periodic signal for use in estimating blood pressure may be acquired from the continuous bio-signal.

The processor 120 may estimate blood pressure by analyzing a waveform of the measured bio-signal. Hereinafter, the term "blood pressure" may refer to any one or any combination of Mean Arterial Pressure (AMP), diastolic blood pressure (DBP), and systolic blood pressure (SBP), unless indicated otherwise. The processor 120 may extract a feature related to blood pressure from the received bio-signal, and may estimate blood pressure by using the extracted feature. However, bio-information is not limited to blood pressure, and the processor 120 may estimate additional bio-information, such as vascular age, arterial stiffness, aortic pressure waveform, stress index, fatigue level, and the like.

A variation in MAP is proportional to cardiac output (CO) and total peripheral resistance (TPR), as shown in the following Equation 1. The CO refers to the amount of blood pumped by the heart in one minute, and may be calculated by multiplying a heart rate by a stroke volume.

$$\Delta MAP = CO \times TPR \quad \text{[Equation 1]}$$

Herein, $\Delta MAP$ denotes a difference in MAP between the left ventricle and the right atrium, in which MAP of the right atrium is generally in a range of 3 mmHg to 5 mmHg, such that the MAP in the right atrium is similar to MAP in the left ventricle or MAP of the upper arm. If absolute actual CO and TPR values are known, MAP may be obtained from the aorta or the upper arm. However, it may be difficult to estimate absolute CO and TPR values based on a bio-signal. Under normal circumstances, the human body has the ability to regulate blood pressure levels. For example, when blood pressure increases due to a rapid increase in CO, the blood vessels are dilated such that the TPR may decrease, thereby allowing blood pressure to return to normal levels.

The processor 120 may extract a feature related to cardiac output (CO) (hereinafter referred to as a "CO feature") and a feature related to total peripheral resistance (TPR) (hereinafter referred to as a "TPR feature") from the bio-signal, and may estimate blood pressure based on the CO feature and the TPR feature. For example, the processor 120 may extract a plurality of characteristic points by analyzing the bio-signal and/or a derivative signal (e.g., a first derivative signal or a second derivative signal) of the bio-signal, and may obtain the CO feature and/or the TPR feature based on one or a combination of two or more of the extracted characteristic points. Here, the CO feature may be a feature value which shows an increasing trend or a decreasing trend in proportion to an actual CO value, wherein the actual CO value changes relative to an actual TPR value, which does not change significantly in a non-stable state compared to a stable state. Further, the TPR feature may be a feature value which shows an increasing trend or a decreasing trend in proportion to an actual TPR value, wherein the actual TPR value changes relative to an actual CO value, which does not change significantly in a non-stable state compared to a stable state.

FIGS. 2A to 2F are diagrams explaining examples of obtaining features related to blood pressure.

Figure 2A:
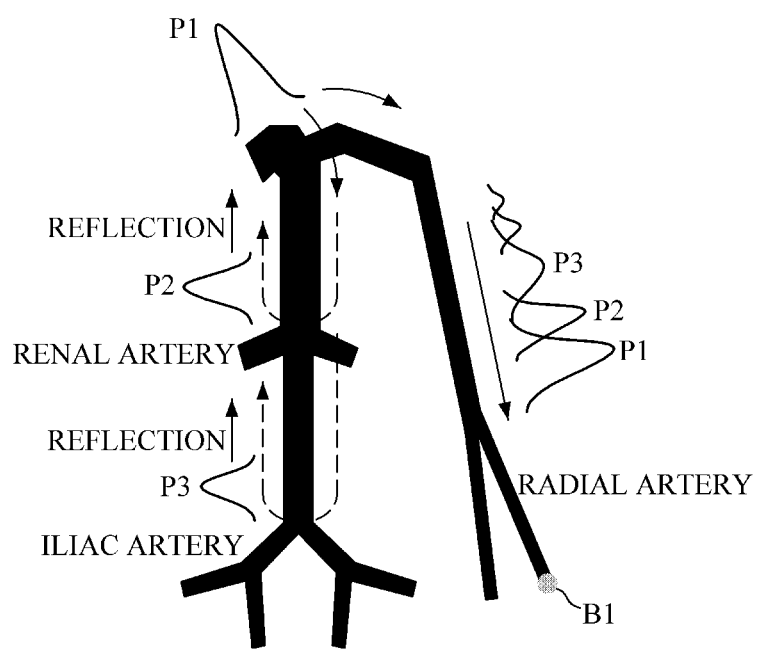
FIGS. 2A to 2F are diagrams explaining examples of obtaining features related to blood pressure.
Figure 2B:
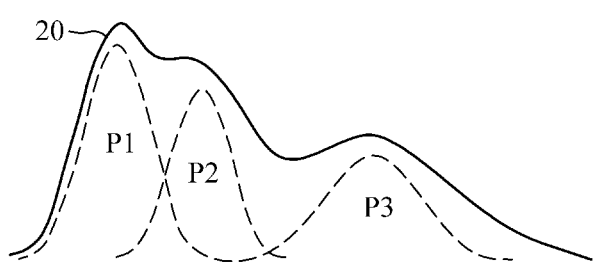

Referring to FIGS. 2A and 2B, a pulse wave signal 20 measured from a peripheral body part B1 may be constituted with a summation of a propagation wave P1 propagating from the heart by blood ejection from the left ventricle to peripheral parts of the body and branching points in the blood vessels, and reflection waves P2 and P3 returning from the peripheral parts of the body or the branching points in the blood vessels. For example, as illustrated in FIGS. 2A and 2B, the waveform of the pulse wave signal is composed of the propagation wave P1 which is generated by blood ejection from the left ventricle, and first and second reflection waves P2 and P3 which are mainly reflected from the renal arteries and the iliac arteries. The propagation wave P1 is related to cardiac characteristics, and the reflection waves P2 and P3 are related to vascular characteristics. Accordingly, based on time points related to the respective constituent pulses P1, P2, and P3 constituting the waveform of the pulse wave signal 20 and/or amplitudes of the pulse weave signal, the processor 120 may extract the CO feature and/or the TPR feature and may measure blood pressure by combining the extracted CO feature and TPR feature.

Figure 2C:
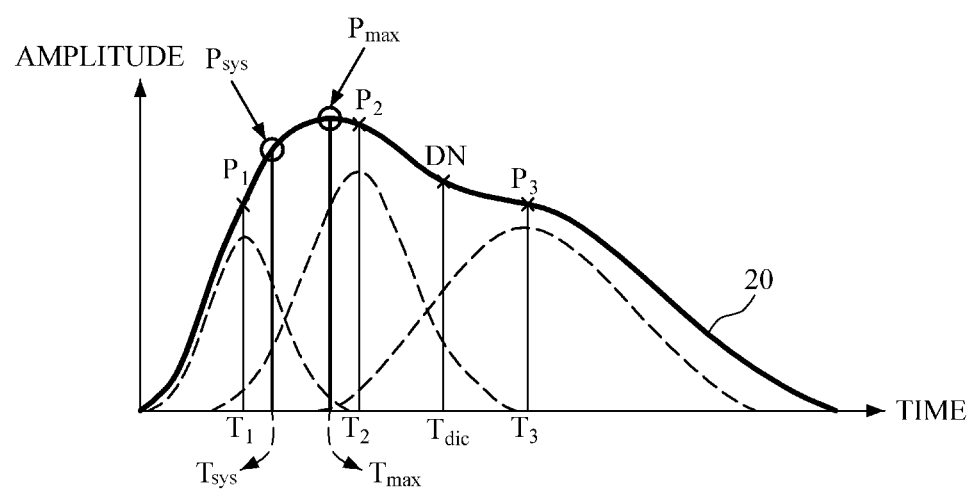
Figure 2D:
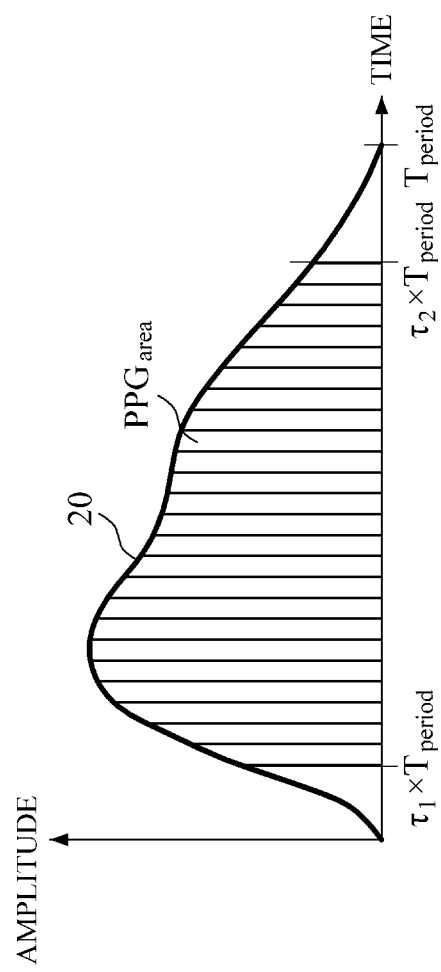

FIGS. 2C and 2D are diagrams illustrating various characteristic points which may be obtained from a bio-signal. The characteristic points illustrated herein are merely examples.

For example, the processor 120 may extract heart rate as a characteristic point from the bio-signal 20. In addition, referring to FIG. 2C, the processor 120 may extract, as characteristic points, a time point T1 and/or an amplitude P1 related to the propagation wave and time points T2 and T3 and/or amplitudes P2 and P3 related to the reflection waves from the bio-signal 20. In particular, the processor 120 may derive a second derivative signal of the bio-signal, and may detect local minimum points of the second derivative signal to extract positions of first, second, and third local minimum points as the time points T1, T2, and T3 of the propagation wave component, the first reflection wave component, and the second reflection wave component.

Further, the processor 120 may extract, as characteristic points, a time point Tmax and/or an amplitude Pmax at a maximum amplitude point in a systolic phase (e.g., an interval from a start point to a point (Tdic) of the dicrotic notch (DN)). In this case, a maximum amplitude point may refer to a point at which a slope is closest to zero in the systolic phase. The processor 120 may derive a first derivative signal of the bio-signal 20, and may extract the point at which the slope is closest to zero by using the first derivative signal. In addition, the processor 120 may extract, as characteristic points, a time point Tsys and/or an amplitude Psys at a middle point between a predetermined position (e.g., a position of a propagation wave component and the maximum amplitude position or at a point where the position of the propagation wave component and the maximum amplitude position are internally divided at a predetermined ratio).

In addition, referring to FIG. 2D, the processor 120 may extract an area PPGarea under a waveform of the bio-signal 20 as a characteristic feature. In particular, the area PPGarea under the waveform may be an area of a portion determined based on a period Tperiod of the bio-signal 20 and random values $\tau_1$ and $\tau_2$. As described above, by adjusting the random values $\tau_1$ and $\tau_2$, the processor 120 may extract, as characteristic points, a total area of the waveform of the bio-signal 20, an area of a predetermined region, e.g., an area of the systolic phase, an area of the diastolic phase, and the like.

Upon extracting the characteristic points, the processor 120 may obtain the CO feature and the TPR feature by using one or an combination of two or more of the extracted characteristic points.

For example, the processor 120 may obtain, as the CO feature, the heart rate HR or a ratio (Pmax/PPGarea) between the amplitude Pmax at the maximum amplitude point and the waveform area PPGarea. However, the CO feature is not limited thereto, and the processor 120 may obtain, as the CO feature, PPGarea, P3/Pmax, P3/Psys, 1/(T3-T1), 1/(T3-Tsys), 1/(T3-Tmax), 1/(T2-T1), P2/P1, P2/Psys, P3/Pmax, P3/P1, and the like.

In addition, the processor 120 may first obtain two or more candidate TPR features, and may obtain one of the two or more candidate TPR features as a final TPR feature. For example, the processor 120 may obtain a first candidate TPR feature (e.g., P2/P1), which is defined as most suited to the TPR feature, and a second candidate TPR feature (e.g., P2/Psys) which changes in a relatively stable manner when compared to the first candidate TPR feature, and may determine one of the first candidate TPR feature and the second candidate TPR feature as the final TPR feature based on a relationship between the first candidate TPR feature and the CO feature. The first candidate TPR feature and the second TPR feature are not limited to the above examples, and may be one of the above examples of the CO feature.

Under normal circumstances, the human body has the ability to regulate blood pressure levels. For example, when blood pressure increases due to a rapid increase in CO, the blood vessels are dilated such that the TPR may decrease; by contrast, when the blood vessels are constricted such that the blood vessels decrease in diameter and TPR increases, the CO may decrease to allow blood pressure to return to normal levels. Accordingly, due to physiological characteristics according to the body's ability to regulate blood pressure levels, the CO feature and the TPR feature have a tendency to change in opposite directions on the whole.

In one embodiment, based on the directionality of change in the CO feature and the first candidate TPR feature at a blood pressure measurement time compared to a calibration time, the processor 120 may determine one of the first candidate TPR feature and the second candidate TPR feature as the TPR feature. In this case, the directionality of change may be defined as a positive direction when the features increase at a current (blood pressure measurement) time compared to the calibration time, and may be defined as a negative direction when the features decrease at the current time compared to the calibration time.

Figure 2E:
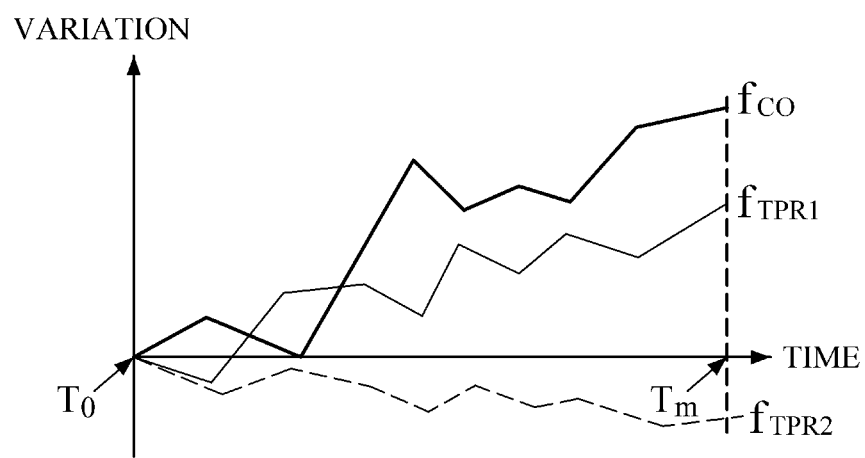
Figure 2F:
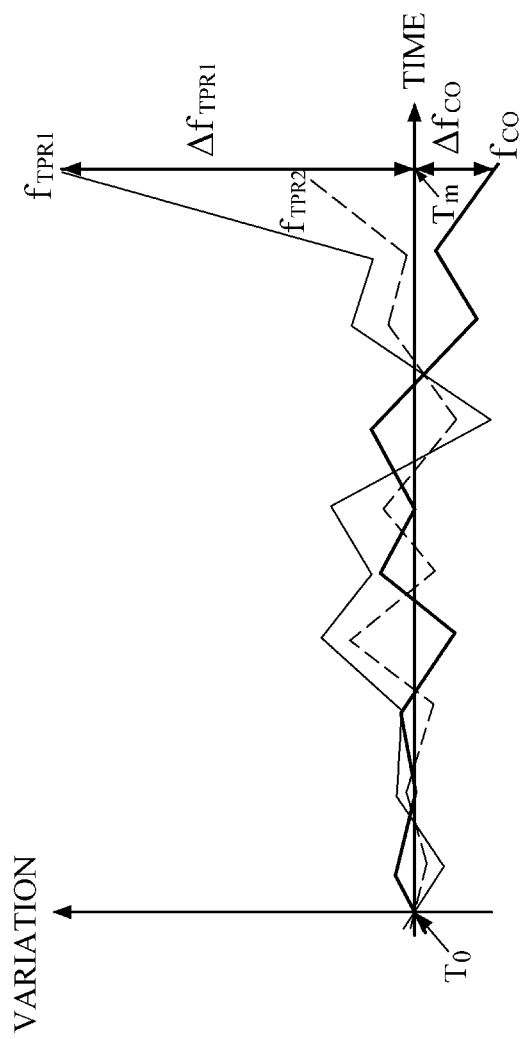

Referring to FIG. 2E, it can be seen that both the CO feature $f_{CO}$ and the first candidate TPR feature $f_{TPR1}$ increase at a current time Tm compared to the calibration time $T_0$, such that the features change in the same positive direction. The processor 120 may determine the second candidate TPR feature $f_{TPR2}$, which changes in a direction opposite to the CO feature $f_{CO}$ and shows a relatively stable variation, as the final TPR feature, so as to be more suited to the ability to regulate blood pressure levels. Unlike the example, FIG. 2F illustrates an example in which the CO feature $f_{CO}$ and the first candidate TPR feature $f_{TPR1}$ change in different directions at the current time Tm compared to the calibration time $T_0$, where the CO feature $f_{CO}$ changes in a negative direction and the first candidate TPR feature $f_{TPR1}$ changes in a positive direction. As described above, when the directions of change are different, the processor 120 may determine the first candidate TPR feature $f_{TPR1}$ as the final TPR feature.

In another example, in the case where the CO feature and the first candidate TPR feature change in different directions, the processor 120 may determine the final TPR feature by further considering a variation in the first candidate TPR feature. For example, as illustrated in FIG. 2F, even when the CO feature $f_{CO}$ and the first candidate TPR feature $f_{TPR1}$ change in different directions, and thus may be suited to physiological characteristics, if a variation $|\Delta f_{TPR1}|$ the first candidate TPR feature $f_{TPR1}$ is excessively greater than a variation $|\Delta f_{CO}|$ in the CO feature $f_{CO}$, the first candidate TPR feature $f_{TPR1}$ may be unstable. Here, the variations $|\Delta f_{TPR1}|$ and $|\Delta f_{co}|$ of the respective features are degrees of change at the current time Tm compared to the calibration time $T_0$, and may be, for example, values normalized by dividing the feature values at the current time by feature values at the calibration time, and by subtracting 1 from the result values.

Accordingly, the processor 120 may compare the variation $|\Delta f_{TPR1}|$ in the first candidate TPR feature $f_{TPR1}$ with a predetermined threshold value, and if the variation is greater than or equal to the threshold value, the processor 120 may determine the second candidate TPR feature $f_{TPR2}$, showing a relatively stable variation, as the final TPR feature; and if not, the processor 120 may determine the first candidate TPR feature $f_{TPR1}$ as the final TPR feature. In this case, the threshold value may be defined as a value $\alpha |\Delta f_{CO}|$ obtained by applying a predetermined weight a to the variation $|\Delta f_{CO}|$ in the CO feature $f_{CO}$. The predetermined weight a may be defined as a value (e.g., 3) greater than 1, and may be a fixed value which may be applied commonly or may be a value personalized for each user.

Upon obtaining the CO feature and the TPR feature, the processor 120 may estimate blood pressure by using a blood pressure estimation model which defines a relationship between the obtained features and blood pressure. The blood pressure estimation model may be predefined as a linear or non-linear function which defines a correlation between the CO feature and the TPR feature and blood pressure. The CO feature and the TPR feature may be obtained for SBP and DBP, respectively. By using the obtained CO feature and TPR feature, the processor 120 may estimate SBP and DBP independently from each other.

In the case in which predetermined calibration conditions are satisfied, the processor 120 may perform calibration to obtain reference information such as the CO feature, the TPR feature, cuff blood pressure, the blood pressure estimation model, and the like. For example, in the case in which there is no reference information required for estimating blood pressure, such as the case in which the apparatus 100 is used for the first time in estimating blood pressure, or the case in which the apparatus 100 is initialized, the processor 120 may first perform calibration. In another example, by analyzing a blood pressure estimation result, the processor 120 may determine whether to perform calibration. For example, when estimation of blood pressure is complete, if an estimated blood pressure value falls outside a predetermined normal range, if a number of times that the estimated blood pressure value falls outside the predetermined normal range is greater than or equal to a threshold value, or if a number of times that the estimated blood pressure value continuously falls outside the predetermined normal range or falls outside a normal range during a predetermined period of time is greater than or equal to a threshold value, the processor 120 may determine that calibration is required. However, the calibration conditions are not limited thereto, and the processor 120 may perform calibration at calibration intervals or in response to a user's request.

Upon determining to perform calibration, the processor 120 may guide a user on the calibration. For example, the processor 120 may guide the user to place an object on a measurement position of the sensor 110, or may guide the user on contact pressure. Further, the processor 120 may control the sensor 110 to acquire a bio-signal, and may obtain the CO feature, the first candidate TPR feature, the second candidate TPR feature, the TPR feature, and the like from the acquired bio-signal, as described above. In addition, by using a communication module included in the apparatus 100, the processor 120 may receive a reference cuff blood pressure from an external device, e.g., a cuff manometer, or may output a user interface on a display to directly receive a reference cuff blood pressure from a user. In addition, the processor 120 may update the blood pressure estimation model by using the obtained CO feature, TPR feature, and reference blood pressure.

Figure 3:
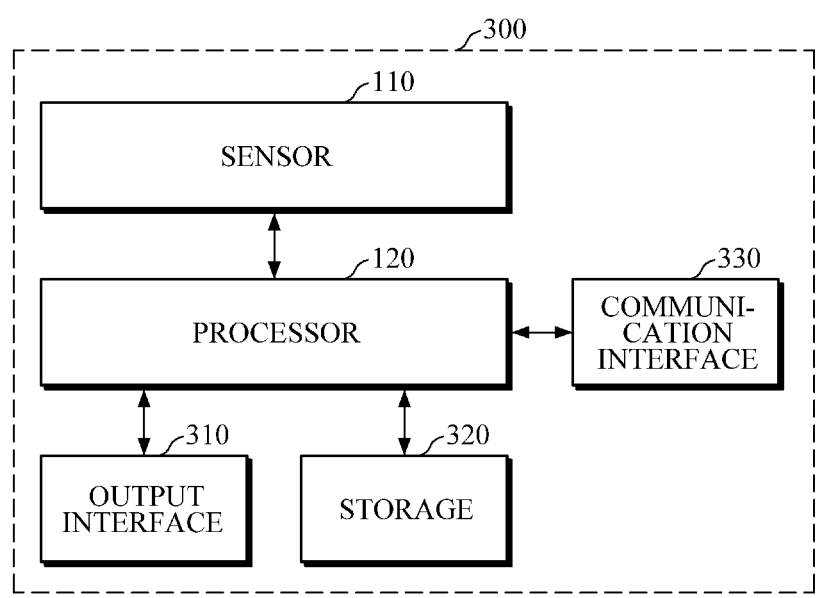
FIG. 3 is a block diagram illustrating an apparatus for estimating blood pressure according to another example embodiment of the present disclosure.

FIG. 3 is a block diagram illustrating an apparatus for estimating blood pressure according to another example embodiment of the present disclosure.

Referring to FIG. 3, an apparatus 300 for estimating blood pressure may include the sensor 110, the processor 120, an output interface 310, a storage 320, and a communication interface 330. The sensor 110 and the processor 120 are described in detail above, and thus a description thereof will be omitted.

The output interface 310 may output the bio-signal, measured by the sensor 110, and/or data generated or processed by the processor 120 by various visual/non-visual methods. The output interface 310 may directly include a display device, a sound device, a haptic device, etc., or may be connected to a display device, a sound device, a haptic device, and the like mounted in an external device through wired and wireless communications.

For example, once a user's blood pressure is estimated, the output interface 310 may output the estimated blood pressure to the display device by using various visual methods, such as by changing color, line thickness, font, etc., based on whether the estimated blood pressure falls within or outside a normal range. In addition, the output interface 310 may output the estimated blood pressure by voice using the sound device, or may output notification as to whether blood pressure is abnormal by vibrations or tactile sensation using the haptic device. Further, by analyzing a blood pressure estimation history, the processor 120 may monitor the user's health condition, in which case the output interface 310 may provide information on actions the user needs to take, such as a warning message, food information that the user should be careful about, hospital appointment information, and the like.

The storage 320 may store reference information obtained during calibration by the processor 120. In addition, the storage 320 may store the bio-signal, CO feature, TPR feature, estimated blood pressure values, etc., which are obtained during estimation of blood pressure. In particular, the reference information may include user information, such as a user's age, gender, occupation, current health condition, etc., and/or the bio-signal, CO feature, TPR feature, reference cuff blood pressure, blood pressure estimation model, etc., which are obtained during calibration, but the reference information is not limited thereto. In particular, the storage 320 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 330 may be connected to an external device by using communication techniques to transmit and receive various data with the external device. For example, the communication interface 330 may receive reference information related to estimating blood pressure, and may transmit the bio-signal, measured by the sensor 110, and the data (e.g., estimated blood pressure value) generated or processed by the processor 120 to the external device. In particular, examples of the external device may include another apparatus for estimating blood pressure, a cuff blood pressure device for measuring cuff blood pressure, a smartphone, a tablet PC, a desktop computer, a laptop computer, etc., but is not limited thereto.

In particular, the communication interface 330 may communicate with the external device by using various wired and wireless communication techniques including Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, third-generation (3G), fourth-generation (4G), fifth-generation (5G), and sixth-generation (6G) communications, and the like. However, the communication techniques are not limited thereto.

Figure 4:
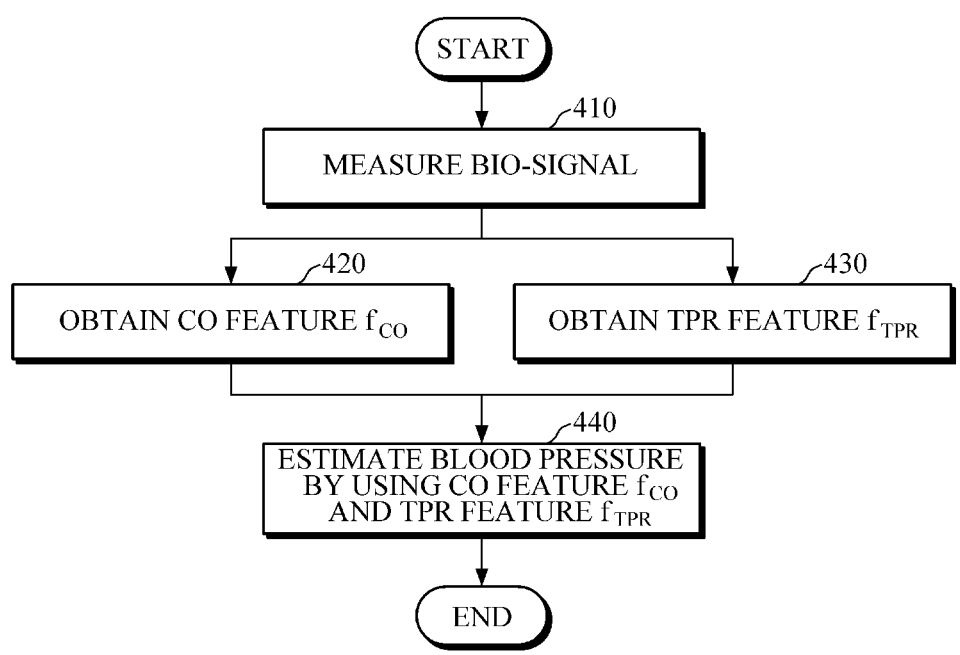
FIG. 4 is a flowchart illustrating a method of estimating blood pressure according to an example embodiment of the present disclosure.

FIG. 4 is a flowchart illustrating a method of estimating blood pressure according to an example embodiment of the present disclosure.

The method of FIG. 4 is an example of a method of estimating blood pressure which is performed by the aforementioned apparatuses 100 and 300 for estimating blood pressure, and will be briefly described below in order to avoid redundancy.

First, in response to a request for estimating blood pressure, the apparatuses 100 and 300 for estimating blood pressure may measure a bio-signal from a user's object in operation 410. Upon receiving a user's request for estimating blood pressure through a user interface or from an external device, or at predetermined intervals, the apparatuses 100 and 300 for estimating blood pressure may measure the bio-signal by driving a light source of a sensor to emit light onto the object and by detecting light scattered or reflected from the object by using a detector.

Then, the apparatuses 100 and 300 for estimating blood pressure may obtain a CO feature by using the bio-signal in operation 420. For example, the apparatuses 100 and 300 for estimating blood pressure may obtain, as the CO feature, heart rate, a ratio between a maximum amplitude in a systolic phase and an area of a waveform of the bio-signal.

Further, the apparatuses 100 and 300 for estimating blood pressure may obtain a TPR feature by using the bio-signal in operation 430. In particular, the apparatuses 100 and 300 for estimating blood pressure may determine a first candidate TPR feature having a high correlation with vascular resistance, and may obtain the TPR feature based on directionality of a change in the first candidate TPR feature and the CO feature obtained in operation 420. The first candidate TPR feature may be defined as, for example, a value obtained by dividing an amplitude of a first reflection wave component by an amplitude of a propagation wave component. Hereinafter, various examples of obtaining the TPR feature will be described with reference to FIGS. 5 to 8.

Subsequently, the apparatuses 100 and 300 for estimating blood pressure may estimate blood pressure by using the CO feature and the TPR feature in operation 440. In particular, the apparatuses 100 and 300 for estimating blood pressure may estimate blood pressure by using a blood pressure estimation model that defines a correlation between a value, obtained by combining the CO feature and the TPR feature, and blood pressure. Upon estimating blood pressure, the apparatuses 100 and 300 for estimating blood pressure may provide a user with information, such as the estimated blood pressure, health condition, warning, response actions, etc., by various visual/non-visual methods.

In an example embodiment, the processor 120 may perform operations 420-440 in real time while the sensor 110 continuously measures the pulse wave signal from the user, in operation 410.

Figure 5:
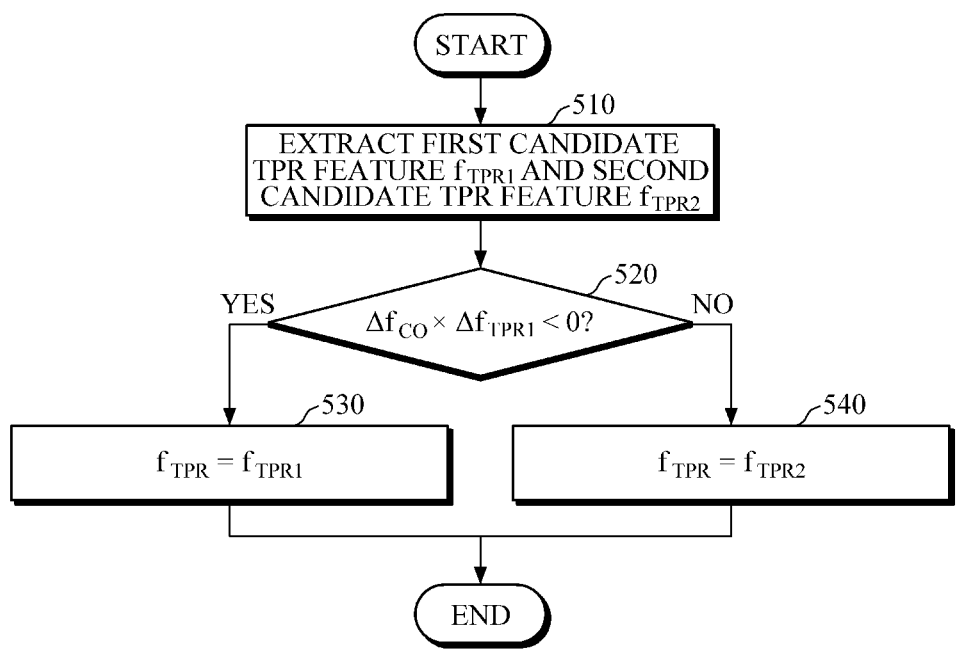
FIGS. 5 to 8 are diagrams illustrating a method of extracting a TPR feature according to example embodiments of the present disclosure.

FIG. 5 is a flowchart illustrating an example of obtaining the TPR feature in operation 430.

First, the apparatuses 100 and 300 for estimating blood pressure may extract the first candidate TPR feature $f_{TPR1}$ and the second candidate TPR feature $f_{TPR2}$ in operation 510. For example, the first candidate TPR feature may be a ratio between the amplitude of the first reflection wave component and the amplitude of the propagation wave. In addition, the second candidate TPR feature may be a ratio between the amplitude of the first reflection wave component and an amplitude at an internally dividing point between a position of the propagation wave component and a maximum amplitude position.

Then, the apparatuses 100 and 300 for estimating blood pressure may determine whether a direction of change in CO feature is the same as a direction of change in TPR feature when compared to a calibration time in operation 520. For example, the apparatuses 100 and 300 for estimating blood pressure may multiply a CO feature variation $\Delta f_{CO}$ and a first candidate TPR feature variation $\Delta f_{TPR1}$, and if a result value is smaller than zero, the apparatuses 100 and 300 for estimating blood pressure may determine that the directions of change are different; and if not, the apparatuses 100 and 300 for estimating blood pressure may determine that the directions of change are the same.

Subsequently, if the directions of change are different, the apparatuses 100 and 300 for estimating blood pressure may determine the first candidate TPR feature $\Delta f_{TPR1}$ as the final TPR feature $f_{TPR}$ in 530. If not, the apparatuses 100 and 300 for estimating blood pressure may determine the second candidate TPR feature $\Delta f_{TPR2}$ as the final TPR feature $f_{TPR}$ in operation 540.

Figure 6:
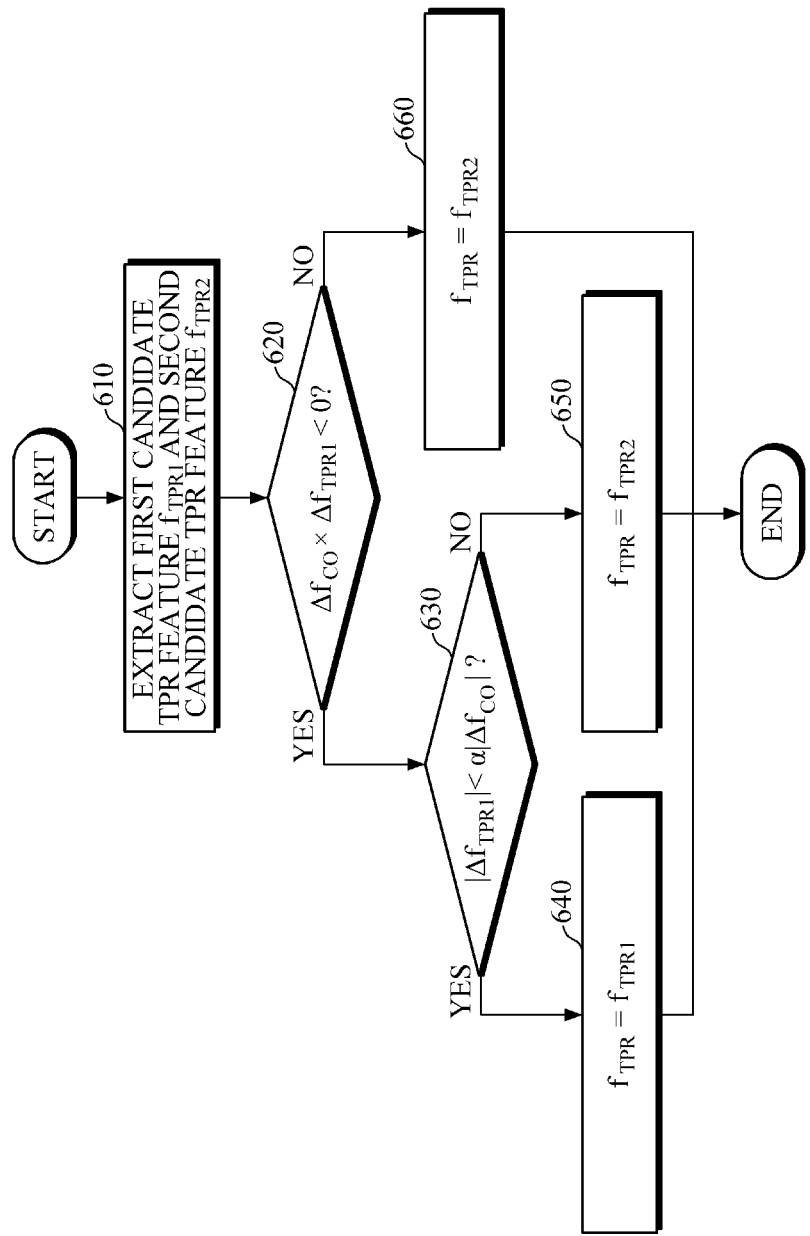

FIG. 6 is a flowchart illustrating another example of obtaining the TPR feature in operation 430.

First, the apparatuses 100 and 300 for estimating blood pressure may extract the first candidate TPR feature $f_{TPR1}$ and the second candidate TPR feature $f_{TPR2}$ from the bio-signal in operation 610.

Based on a determination of whether a product of the CO feature variation $\Delta f_{CO}$ and the first candidate TPR feature variation $\Delta f_{TPR1}$ is smaller than zero, the apparatuses 100 and 300 for estimating blood pressure may determine whether the directions of change in the features are the same in operation 620.

Subsequently, if the product of the CO feature variation $\Delta f_{CO}$ and the first candidate TPR feature variation $\Delta f_{TPR1}$ is smaller than zero, such that the directions of change are different, the apparatuses 100 and 300 for estimating blood pressure may determine whether an absolute value $|\Delta f_{TPR1}|$ of the variation in the first candidate TPR feature is smaller than a predetermined threshold value $\alpha|\Delta f_{CO}|$ in operation 630.

Next, if the absolute value of the variation in the first candidate TPR feature is smaller than the predetermined threshold value, the apparatuses 100 and 300 for estimating blood pressure may determine the first candidate TPR feature $f_{TPR1}$ as the final TPR feature $f_{TPR}$ in operation 640; and if not, the apparatuses 100 and 300 for estimating blood pressure may determine the second candidate TPR feature $f_{TPR2}$ as the final TPR feature $f_{TPR}$ in operation 650.

If the product of the CO feature variation $\Delta f_{CO}$ and the first candidate TPR feature variation $\Delta f_{TPR1}$ is not smaller than zero in operation 630, the apparatuses 100 and 300 for estimating blood pressure may determine the second candidate TPR feature $f_{TPR2}$ as the final TPR feature $f_{TPR}$ in operation 660.

Figure 7:
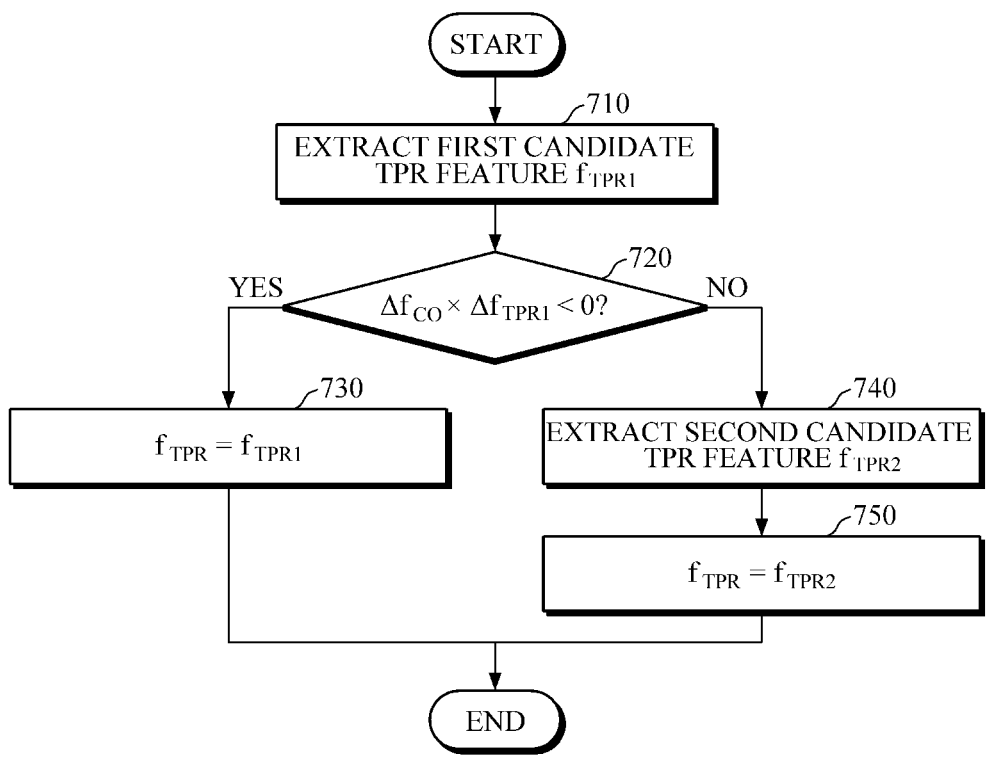

FIG. 7 is a flowchart illustrating yet another example of obtaining the TPR feature in operation 430.

First, the apparatuses 100 and 300 for estimating blood pressure may extract the first candidate TPR feature $f_{TPR1}$ from the bio-signal in operation 710.

Then, the apparatuses 100 and 300 for estimating blood pressure may determine whether a direction of change in the CO feature is the same as a direction of change in the first candidate TPR feature when compared to a calibration time in operation 720.

Subsequently, if the directions of change are different, the apparatuses 100 and 300 for estimating blood pressure may determine the first candidate TPR feature $f_{TPR1}$ as the final TPR feature $f_{TPR}$ in operation 730; and if not, the apparatuses 100 and 300 for estimating blood pressure may extract the second candidate TPR feature $f_{TPR2}$ in operation 740 and determine the extracted second candidate TPR feature $f_{TPR2}$ as the final TPR feature $f_{TPR}$ in operation 750.

Figure 8:
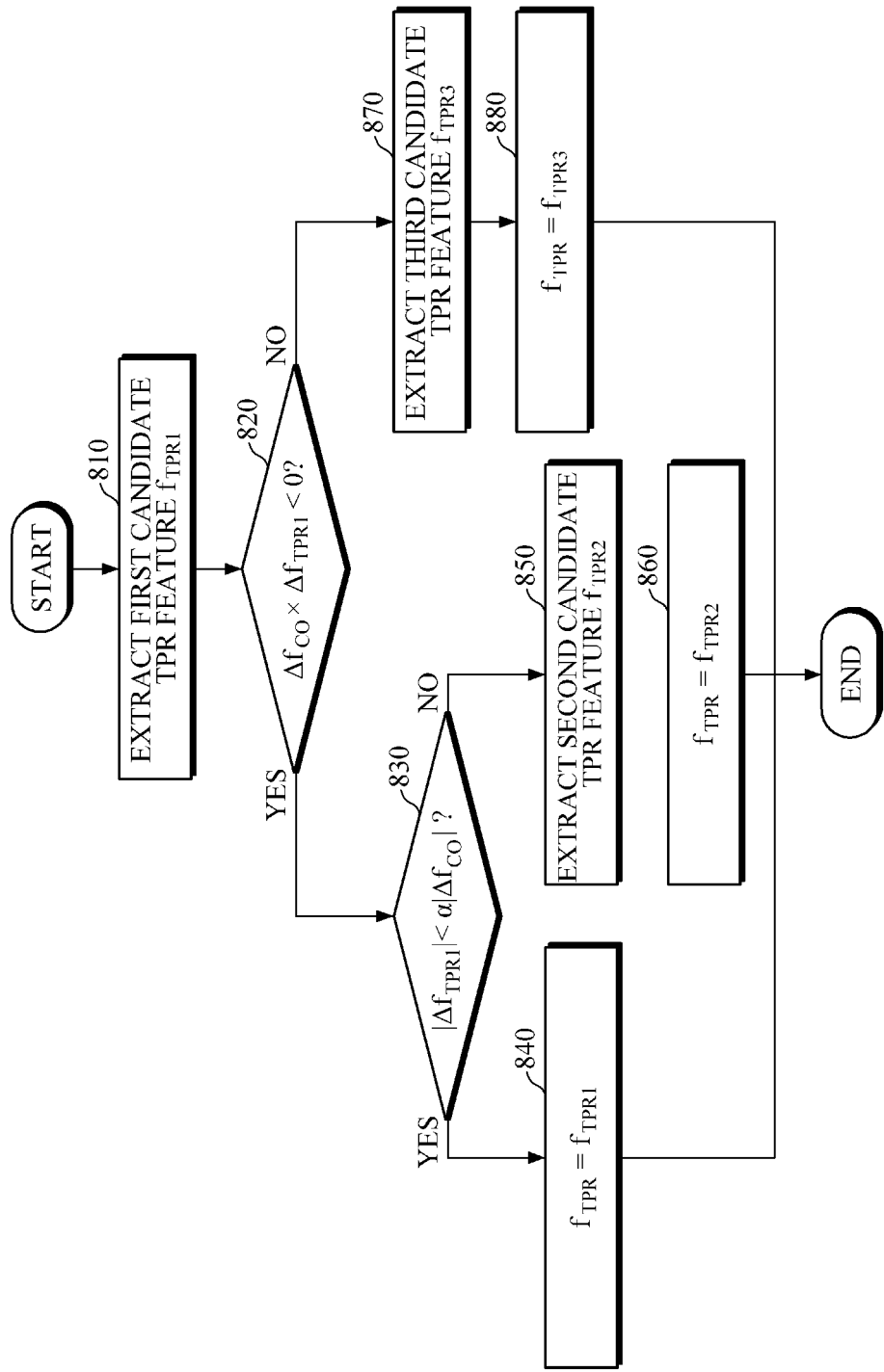

FIG. 8 is a flowchart illustrating still another example of obtaining the TPR feature in operation 430.

First, the apparatuses 100 and 300 for estimating blood pressure may extract the first candidate TPR feature $f_{TPR1}$ from the bio-signal in operation 810.

Then, the apparatuses 100 and 300 for estimating blood pressure may determine whether a direction of change in the CO feature is the same as a direction of change in the first candidate TPR feature when compared to a calibration time in operation 820.

Next, if the directions of change are different, the apparatuses 100 and 300 for estimating blood pressure may determine whether an absolute value $|\Delta f_{TPR1}|$ of the variation in the first candidate TPR feature is smaller than a predetermined threshold value $\alpha|\Delta f_{CO}|$ in operation 830, and if the absolute value is smaller than the predetermined threshold value, the apparatuses 100 and 300 for estimating blood pressure may determine the first candidate TPR feature $f_{TPR1}$ as the final TPR feature $f_{TPR}$ in 840; and if not, the apparatuses 100 and 300 for estimating blood pressure may extract the second candidate TPR feature $f_{TPR2}$ in operation 850 and may determine the second candidate TPR feature $f_{TPR2}$ as the final TPR feature $f_{TPR}$ in operation 860.

If the directions of change are the same in 820, the apparatuses 100 and 300 for estimating blood pressure may extract a third candidate TPR feature $f_{TPR3}$ in operation 870 and may determine the extracted third candidate TPR feature $f_{TPR3}$ as the final TPR feature $f_{TPR}$ in operation 660. In particular, the third candidate TPR feature $f_{TPR3}$ may be the same value as the second candidate TPR feature $f_{TPR2}$, or a value showing a relatively stable variation compared to the second candidate TPR feature.

Figure 9:
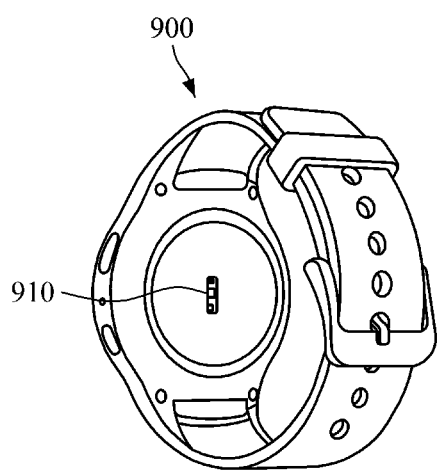
FIGS. 9 to 11 are block diagrams illustrating various structures of an electronic device including an apparatus for estimating blood pressure.
Figure 10:
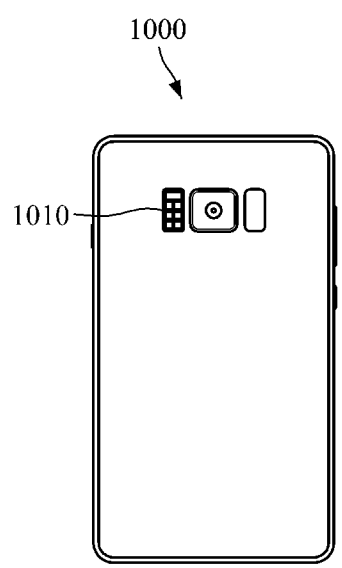
Figure 11:
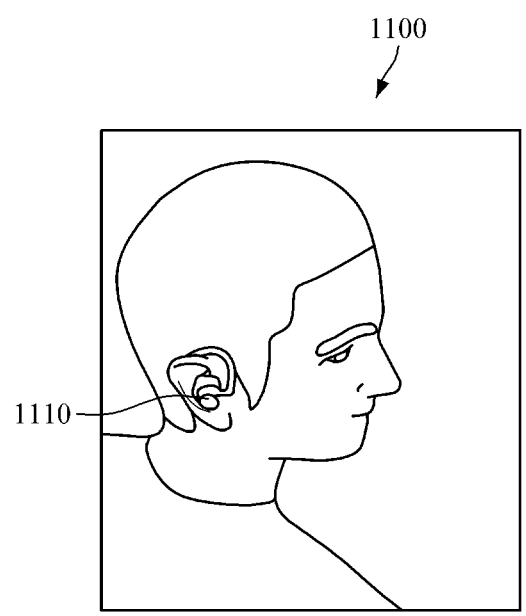

FIGS. 9 to 11 are block diagrams illustrating various structures of an electronic device including the apparatus 100 or 300 for estimating bio-information of FIG. 1 or FIG. 3.

The electronic device may include, for example, various types of wearable devices, e.g., a smart watch, a smart band, smart glasses, smart earphones, a smart ring, a smart patch, and a smart necklace, and a mobile device such as a smartphone, a tablet PC, etc., or home appliances or various Internet of Things (IoT) devices (e.g., home IoT device, etc.) based on Internet of Things (IoT) technology.

The electronic device may include a sensor device, a processor, an input device, a communication module, a camera module, an output device, a storage device, and a power module. All the components of the electronic device may be integrally mounted in a specific device or may be distributed in two or more devices. The sensor device may include the sensor (e.g., PPG sensor) of the apparatuses 100 and 300 for estimating bio-information, and may further include an additional sensor, such as a gyro sensor, a Global Positioning System (GPS), and the like.

The processor may execute programs, stored in the storage device, to control components connected to the processor, and may perform various data processing or computation, including estimation of bio-information (e.g., blood pressure). For example, the processor may evaluate the quality of a PPG signal, measured by using the PPG sensor of the sensor device, and may estimate blood pressure based on the evaluation result. Various embodiments of estimating blood pressure are described above, such that a detailed description thereof will be omitted. The processor may include a main processor, e.g., a central processing unit (CPU) or an application processor (AP), etc., and an auxiliary processor, e.g., a graphics processing unit (GPU), an image signal processor (ISP), a sensor hub processor, or a communication processor (CP), etc., which is operable independently from, or in conjunction with, the main processor.

The input device may receive a command and/or data to be used by each component of the electronic device, from a user and the like. The input device may include, for example, a microphone, a mouse, a keyboard, or a digital pen (e.g., a stylus pen, etc.).

The communication module may support establishment of a direct (e.g., wired.) communication channel and/or a wireless communication channel between the electronic device and other electronic device, a server, or the sensor device within a network environment, and performing of communication via the established communication channel. The communication module may include one or more communication processors that are operable independently from the processor and supports a direct communication and/or a wireless communication. The communication module may include a wireless communication module, e.g., a cellular communication module, a short-range wireless communication module, or a global navigation satellite system (GNSS) communication module, etc., and/or a wired communication module, e.g., a local area network (LAN) communication module, a power line communication (PLC) module, and the like. These various types of communication modules may be integrated into a single chip, or may be separately implemented as multiple chips. The wireless communication module may identify and authenticate the electronic device in a communication network by using subscriber information (e.g., international mobile subscriber identity (DASD, etc.) stored in a subscriber identification module.

The camera module may capture still images or moving images. The camera module may include a lens assembly having one or more lenses, image sensors, image signal processors, and/or flashes. The lens assembly included in the camera module may collect light emanating from a subject to be imaged.

The output device may visually/non-visually output data (e.g., estimated blood pressure values, health condition, warning, actions, etc.) generated or processed by the electronic device. The output device may include a sound output device, a display device, an audio module, and/or a haptic module.

The sound output device may output sound signals to the outside of the electronic device. The sound output device may include a speaker and/or a receiver. The speaker may be used for general purposes, such as playing multimedia or playing record, and the receiver may be used for incoming calls. The receiver may be implemented separately from, or as part of, the speaker.

The display device may visually provide information to the outside of the electronic device. The display device may include, for example, a display, a hologram device, or a projector and control circuitry to control the devices. The display device may include touch circuitry adapted to detect a touch, and/or sensor circuitry pressure sensor, etc.) adapted to measure the intensity of force incurred by the touch.

The audio module may convert a sound into an electrical signal or vice versa. The audio module may obtain the sound via the input device, or may output the sound via the sound output device, and/or a speaker and/or a headphone of another electronic device directly or wirelessly connected to the electronic device.

The haptic module may convert an electrical signal into a mechanical stimulus (e.g., vibration, motion, etc.) or electrical stimulus which may be recognized by a user by tactile sensation or kinesthetic sensation. The haptic module may include, for example, a motor, a piezoelectric element, and/or an electric stimulator.

The storage device may store driving conditions required for driving the sensor device, and various data required for other components of the electronic device. The various data may include, for example, software and input data and/or output data for a command related thereto. The storage device may include a volatile memory and/or a non-volatile memory.

The power module may manage power supplied to the electronic device. The power module may be implemented as part of, for example, a power management integrated circuit (PMIC). The power module may include a battery, which may include a primary cell which is not rechargeable, a secondary cell which is rechargeable, and/or a fuel cell.

Referring to FIG. 9, the electronic device may be implemented as a wristwatch wearable device 900, and may include a main body and a wrist strap. A display is provided on a front surface of the main body, and may display various application screens, including time information, received message information, and the like. A sensor device 910 may be disposed on a rear surface of the main body.

Referring to FIG. 10, the electronic device may be implemented as a mobile device 1000 such as a smartphone.

The mobile device 1000 may include a housing and a display panel. The housing may form an exterior of the mobile device 1000. The housing has a first surface, on which a display panel and a cover glass may be disposed sequentially, and the display panel may be exposed to the outside through the cover glass. A sensor device 1010, a camera module and/or an infrared sensor, and the like may be disposed on a second surface of the housing. The processor and various other components may be disposed in the housing.

Referring to FIG. 11, the electronic device may be implemented as an ear-wearable device 1100.

The ear-wearable device 1100 may include a main body and an ear strap. A user may wear the ear-wearable device 1100 by hanging the ear strap on the auricle. The ear strap may be omitted depending on a shape of the ear-wearable device 1100. The main body may be inserted into the external auditory meatus. A sensor device 1110 may be mounted in the main body. Further, the processor may be disposed in the main body, and may estimate blood pressure by using a PPG signal measured by the sensor device 1110. Alternatively, the ear-wearable device 1100 may estimate blood pressure by interworking with an external device. For example, the ear-wearable device 1100 may transmit the pulse wave signal, measured by the sensor device 1110 of the ear-wearable device 1100, to an external device, e.g., a mobile device, a tablet PC, etc., through a communication module provided in the main body, so that a processor of the external device may estimate blood pressure, and may output the estimated blood pressure value through a sound output module provided in the main body of the ear-wearable device 1100.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general—use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing example embodiments are merely exemplary and are not to be construed as limiting. The present teaching can be readily applied to other types of apparatuses. Also, the description of the example embodiments is intended to be illustrative, and not to limit the scope of the claims, and many alternatives, modifications, and variations will be apparent to those skilled in the art.

What is claimed is:

1. An apparatus for estimating blood pressure, the apparatus comprising:
   a memory storing one or more instructions; and
   a processor configured to execute the one or more instructions to:
   extract a cardiac output (CO) feature, a first candidate total peripheral resistance (TPR) feature, and a second candidate TPR feature from a bio-signal;
   determine one of the first candidate TPR feature and the second candidate TPR feature as a TPR feature based on a direction of change in the CO feature and a direction of change in the first candidate TPR feature between a blood pressure measurement time and a calibration time; and
   estimate the blood pressure based on the TPR feature and the CO feature.

2. The apparatus of claim 1, wherein the CO feature comprises at least one of a heart rate, and a ratio between an amplitude at a predetermined point and an area under a waveform of the bio-signal.

3. The apparatus of claim 2, wherein the predetermined point comprises a point at which a slope of the waveform of the bio-signal is closest to zero in a systolic phase.

4. The apparatus of claim 1, wherein the first candidate TPR feature comprises a ratio between an amplitude of a propagation wave component and an amplitude of a reflection wave component of the bio-signal, and
wherein the second candidate TPR feature comprises a ratio between the amplitude of the reflection wave component and an amplitude at an internally dividing point between a point of the propagation wave component and a predetermined point of the bio-signal.

5. The apparatus of claim 4, wherein the processor is further configured to obtain a second derivative signal of the bio-signal; and detect local minimum points of the second derivative signal as the point of the propagation wave component and a point of the reflection wave component.

6. The apparatus of claim 1, wherein in response to the direction of change in the CO feature being different from the direction of change in the first candidate TPR feature, the processor is further configured to determine the first candidate TPR feature as the TPR feature, and in response to the directions of change being identical, the processor is further configured to determine the second candidate TPR feature as the TPR feature.

7. The apparatus of claim 1, wherein:
in response to the direction of change in the CO feature being different from the direction of change in the first candidate TPR feature, and a variation in the first candidate TPR feature being less than a predetermined threshold value, the processor is further configured to determine the first candidate TPR feature as the TPR feature;
in response to the direction of change in the CO feature being different from the direction of change in the first candidate TPR feature, and the variation in the first candidate TPR feature being greater than or being equal to the predetermined threshold value, the processor is further configured to determine the second candidate TPR feature as the TPR feature; and
in response to the direction of change in the CO feature being identical to the direction of change in the first candidate TPR feature, the processor is further configured to determine the second candidate TPR feature as the TPR feature.

8. The apparatus of claim 7, wherein the predetermined threshold value comprises a value obtained by applying a predetermined weight to a variation in the CO feature.

9. The apparatus of claim 8, wherein the processor is further configured to determine:
the variation in the first candidate TPR feature by dividing the first candidate TPR feature value at the blood pressure measurement time by a reference TPR feature value at the calibration time, to obtain a first division result, and by subtracting 1 from the first division result; and
the variation in the CO feature by dividing the CO feature value at the blood pressure measurement time by a reference CO feature value at the calibration time, to obtain a second division result, and by subtracting 1 from the second division result.

10. The apparatus of claim 8, wherein the processor is further configured to estimate the blood pressure by applying a predefined blood pressure estimation model to a result obtained by combining the CO feature and the TPR feature.

11. A method of estimating blood pressure, the method comprising:
measuring a bio-signal from an object;
extracting a cardiac output (CO) feature, a first candidate total peripheral resistance (TPR) feature, and a second candidate TPR feature based on the bio-signal;
determining one of the first candidate TPR feature and the second candidate TPR feature as a TPR feature based on a direction of change in the CO feature and a direction of change in the first candidate TPR feature between a blood pressure measurement time and a calibration time; and
estimating the blood pressure based on the TPR feature and the CO feature.

12. The method of claim 11, wherein the CO feature comprises at least one of a heart rate, and a ratio between an amplitude at a predetermined point and an area under a waveform of the bio-signal.

13. The method of claim 12, wherein the predetermined point comprises a point at which a slope of the waveform of the bio-signal is closest to zero in a systolic phase.

14. The method of claim 11, wherein the first candidate TPR feature comprises a ratio between an amplitude of a propagation wave component and an amplitude of a reflection wave component of the bio-signal, and
wherein the second candidate TPR feature comprises a ratio between the amplitude of the reflection wave component and an amplitude at an internally dividing point between a point of the propagation wave component and a predetermined point of the bio-signal.

15. The method of claim 11, wherein the determining of the TPR feature comprises, in response to the direction of change in the CO feature being different from the direction of change in the first candidate TPR feature, determining the first candidate TPR feature as the TPR feature, and in response to the directions of change being identical, determining the second candidate TPR feature as the TPR feature.

16. The method of claim 11, wherein the determining of the TPR feature comprises:
in response to the direction of change in the CO feature being different from the direction of change in the first candidate TPR feature, and a variation in the first candidate TPR feature being less than a predetermined threshold value, determining the first candidate TPR feature as the TPR feature;
in response to the direction of change in the CO feature being different from the direction of change in the first candidate TPR feature, and the variation in the first candidate TPR feature being greater than or being equal to the predetermined threshold value, determining the second candidate TPR feature as the TPR feature; and
in response to the direction of change in the CO feature being identical to the direction of change in the first candidate TPR feature, determining the second candidate TPR feature as the TPR feature.

17. The method of claim 16, wherein the predetermined threshold value comprises a value obtained by applying a predetermined weight to the variation in the CO feature.

18. The method of claim 11, wherein the estimating of the blood pressure comprises estimating the blood pressure by applying a predefined blood pressure estimation model to a result obtained by combining the CO feature and the TPR feature.

19. An electronic device comprising:
a main body;
a photoplethysmogram (PPG) sensor configured to measure a PPG signal from an object; and
a processor configured to:
extract a cardiac output (CO) feature and a first candidate total peripheral resistance (TPR) feature from the PPG signal;
determine a TPR feature based on whether a direction of change in the CO feature is identical to a direction of change in the first candidate TPR feature between a blood pressure measurement time and a calibration time; and estimate blood pressure based on the TPR feature and the CO feature.

20. The electronic device of claim 19, wherein in response to the direction of change in the CO feature being different from the direction of change in the first candidate TPR feature, the processor is further configured to determine the first candidate TPR feature as the TPR feature, and in response to the directions of change being identical, the processor is further configured to extract a second candidate TPR feature, having a less variation than the first candidate TPR feature between the blood pressure measurement time and the calibration time, as the TPR feature.

* * * * *